United States Patent [19]
Santini

[11] Patent Number: 6,039,266
[45] Date of Patent: Mar. 21, 2000

[54] METHOD AND APPARATUS FOR DISPENSING VOLATILE COMPONENTS OF AN AIR TREATING GEL

[75] Inventor: Thomas F. Santini, Allentown, N.J.

[73] Assignee: Wessel Fragrances, Inc., Englewoods Cliffs, N.J.

[21] Appl. No.: 09/203,845

[22] Filed: Dec. 2, 1998

[51] Int. Cl.[7] .................................................. A61L 9/12
[52] U.S. Cl. .................................................. 239/60
[58] Field of Search .................................. 239/6, 34, 57, 239/60

[56] References Cited

U.S. PATENT DOCUMENTS 4,809,912  3/1989  Santini ............................... 239/60 X
5,060,858  10/1991  Santini .................................. 239/60

*Primary Examiner*—Lesley D. Morris
*Attorney, Agent, or Firm*—Davis and Bujold

[57] ABSTRACT

A dispenser for dispensing volatile components of an air treating gel, which stabilizes an emanating surface of an emanating face of an enclosed air treating gel, that is structurally simple and relatively easy to manufacture. The emanating surface of the gel attaches to a grille of an aperture member fast within and adjacent a major opening of the dispenser. The aperture member is designed to support the emanating surface continuously throughout the dispensation of the volatile components and may be sized to provide vacuum relief to a bottom surface of the enclosed gel. Accordingly, the emanating surface is replenished from a reservoir of gel within the dispenser while remaining supported by the aperture member.

11 Claims, 5 Drawing Sheets

METHOD AND APPARATUS FOR DISPENSING VOLATILE COMPONENTS OF AN AIR TREATING GEL

FIELD OF THE INVENTION

This invention is directed to a dispensing device, and more particularly, to dispensing devices and methods for the evaporative delivery of volatilizable air treating agents contained within aqueous based solidified gel reservoirs. These volatilizable agents might be represented by a fragrance, odor counteractant, insecticide, insect attractant, pharmaceutical agent and the like. This invention has particular application for use with so called continuous action air freshening units and will be described in connection with such application, although other applications will be obvious to those persons skilled in the art.

BACKGROUND OF THE INVENTION

Such solidified, erodible, aqueously based, airtreating gel reservoirs have had a long history of use as a means from which to deliver volatilizable air treating materials due to their economy, ease of manufacture and their effectiveness in gradually introducing those materials into the air for the purpose of creating a fragrance awareness.

However, this methodology is also accompanied by a number of disadvantages including a tendency for syneresis, unsightly appearance of the shrunken gel residue, uncontrolled and inefficient rates of release and large differences in size between a new and spent reservoir, resulting in an emanating surface which continually diminishes in size. Solid air treating gels are predominantly aqueous compositions and as such are characterized by a high degree of erodibility as evidenced by their large change in size as they become depleted overtime. Typically, units are on the order of 150–250 grams in weight and as a result, represent one of the larger sized options available in the area of continuous action sustained release fragrance methodologies. Depending upon such factors as air movement, humidity, and temperature, as well as the area of exposure set by the consumer, these units routinely last from three to six weeks. The physical change in size of the eroding reservoir typically results in a perceptible disparity in performance between newly opened units and those which might have been opened and exposed for only one week.

Originally, these types of gels were preformed into blocks or cast directly into vacuum-formed plastic containers. More recently, however, numerous types of container options have become available which encase the gel as well as offer some degree of control over the rate of release of the air treating components from the gel reservoir. Typically, such containers consist of two parts, a base and a cover housing which can either be raised or lowered to expose all or a desired portion of the gel reservoir. This configuration thus offers some influence over the rate of release of volatilizables from the unit. To this end, numerous modifications have been made not only in the options available in the gel composition, but also in the design of the dispenser. These improvements have all been directed at addressing some of the more significant shortcomings typically associated with this method of dispensing.

The use of gels and their long history of development can be seen in such prior art as U.S. Pat. No. 2,466,146 (Baker) which details the use of a number of hydrocolloids for the purpose of preparing elastic gels.

U.S. Pat. No. 3,945,950 (Vosganiantz) describes the use of a substantial percentage of a volatilizable water-soluble glycol ether into the gel formulation in order to provide for a more regulated release from the solid gel composition.

U.S. Pat. No. 4,056,612 (Lin) details the development of air freshening gels which exhibit essentially no syneresis as well as improved gel strength through the use of an ammonium salt as part of the gel formulation.

U.S. Pat. No. 4,178,264 (Streit et al.) demonstrates the use of metallic stearates as a formulation enhancement for improving the thermal stability of carrageenan-based gel air freshening systems.

Similarly, the development of the dispenser for air treating gels also has shown a history of continual improvement.

U.S. Pat. Nos. 2,878,060 and 3,239,145 (Russo) demonstrate the use of a cylindrical and telescoping dispenser which provides a means of adjustability in combination with an integral seal which prevents the loss of vapor during periods of non use.

U.S. Pat. No. 3,908,906 (Crowe et al.) further develops an easily-fabricated loadable container which provides the option of adjustability with an integral sealing mechanism.

U.S. Pat. No. 3,910,495 (Cummings, et al.) details the development of an adjustable gel housing with a vapor-tight seal and the need for fewer operations in the molding of the container housing.

Air treating gels typically use a hydrocolloid as a gelling agent at concentrations ranging from 0.75% to 4% with an aqueous concentration which frequently approaches 90% in conjunction with an air treating component between 1% and 5%. In addition, the aqueous concentration of the gel formulation can contain co-solvents which provide increased solubility for the particular essential oils and fragrances dispersed within the aqueous medium. These co-solvents are typically used at a concentration of between 2% and 6% and are represented by such materials as propylene glycol, dipropylene glycol, hexylene glycol, dipropylene glycol methyl ether and ethanol or the like. It can easily be seen based on this composition that the co-evaporation of water with volatile air treating agents results in a reservoir with a high concentration of volatilizables and as such is accompanied by a high degree of shrinkage. The continued reduction in this reservoir size results in a smaller emanating surface and a diminished interface between this gel releasing surface and the surrounding atmosphere. This contributes to a reduction in the diffusion rate of the co-evaporants and a significant disparity in the performance of the unit as measured by its ability to create a fragrance awareness. Typically, these devices perform well when newly opened but noticeably decline in their effectiveness upon further use thereof. This limitation has frequently been cited as a major shortcoming of this technology and has been a primary reason why this delivery system has not found greater acceptability and application. As previously noted, the prior art has continued to improve the nature of the gel composition used in these reservoirs as well as to further develop the packaging. Little, however, has been done in the methodology to develop a device with a more consistent sustained effectiveness in the presence of a continually diminishing reservoir size.

My prior U.S. Pat. No. 4,809,912, in an effort to exert more influence over the rate of release of a gel dispensing system, details an alternative methodology and device to the above mentioned prior art. The unit of the '912 patent employs a rate controlling membrane disposed over the primary opening at the top of a gel container housing. During filling, heated and liquified air freshening gel is introduced through a fill hole at the bottom of an inverted container onto a porous covering membrane. The gel upon cooling, solidifies and becomes intimately attached to this membrane. The membrane provides support by which the emanating surface of the gel in contact with the membrane is kept dimensionally intact, such that the normal tendency of the gel to shrink inward is negated. The uniformity in the surface area of the emanating face of the gel in contact with the membrane contributes to a more uniform rate of diffusion throughout the functional life of the device.

In a similar effort to maintain a more dimensionally stable emanating surface, the dispenser of my U.S. Pat. No. 5,060,858 uses a narrow absorbent band or some mechanical means of attachment that are positioned at the perimeter of the gel container adjacent its primary opening. Again, in a bottom fill procedure, heated liquified gel engages the absorbent band or the mechanical means at the top of the container, and upon cooling, that gel portion contacting the porous band or mechanical means becomes essentially fixed in place and immobilized. When a dispenser of the '858 patent is activated, the gel portion, which is anchored in place, is not permitted to shrink inward, whereas the gel beneath this segment continually shrinks from the bottom upward towards the emanating surface. Eventually, the entire reservoir moves upward and depletes itself leaving only a residue in the segment anchored to the container. The benefit of the '858 technology is once again the stabilization of the emanating surface such that it remains dimensionally unchanged and provides a more uniform fragrance transmission.

However, my attempts to improve the air treating performance, although providing a more controlled rate of release, require more packaging components and an increased number of assembly operations prior to filling. Accordingly, there is still a need for an improved air treating device, which stabilizes the emanating surface of the emanating face of the enclosed air treating gel, that is also structurally simple and relatively easy to manufacture.

SUMMARY OF THE INVENTION

The present invention provides a method and apparatus for dispensing volatile components of an air treating gel which overcome the aforementioned problems and drawbacks associated with the prior art designs.

It is the object of the present invention, to provide a novel method for the continuous release of volatilizable air treating materials, from an evaporative device utilizing a solid gel reservoir, such that the emanating surface of such gel reservoir remains essentially unchanged over the functional life of the unit.

Another object of the present invention is to provide a device which utilizes an aqueous based gel air treating reservoir exhibiting improved fragrance transmission during its functional life.

It is a further object of the present invention to provide a dispensing container for air treating gels, which is structurally simple, relatively easy to manufacture and requires very few assembly steps prior to filling.

In addition, an object of the present invention is to provide a method of allowing vacuum relief, within the container, without relying upon a preformed channel within the package.

Finally, it is primarily an object of the present invention to detail a continuous action vapor dispensing device which employs an apertured member (grid or grille) which is lockably inserted into the container and disposed horizontally in a plane substantially flush with the primary opening of the gel housing.

Accordingly, the present invention describes an improved and simplified dispenser for solid air treating gels and defines a process which allows the volatile compositions of matter, in a gel reservoir, to diffuse into the surrounding atmosphere. It is the elastic flexible nature of hydrocolloid based air freshener gels which makes this type of gel so singularly well suited to the dispenser disclosed herein. The operative process in this device involves the movement of the fugitive materials in the air treating gel to continually migrate upward through the gel and past the grille member in route to the emanating surface where they evaporate into the atmosphere. The continuous depletion of the large concentration of volatilizables (water, fragrance) from the gel matrix results in the constant shrinking in size of the reservoir which slowly collapses overtime onto the immobilized segment of the gel as created by the presence of the grille. In this context, it is readily apparent that there is no movement of the gel past the grille rather just the passage of the volatile components of the gel reservoir which easily pass through it. The gel segment anchored in place by the grille and which includes the emanating surface, remains essentially intact and unchanged throughout the functional life of the device. In contrast, the gel residing beneath the grille, contained in the gel housing, continually draws itself upward as the structural support provided, in large part by the water, to the formed gel becomes depleted and the gum residue and non-volatile constituents of the gel composition collapse toward the immobilized gel segment, due to the evaporative loss of this primary support constituent. Typically, preferred gel forming agents of the type suitable for preparing elastic solid gel reservoirs include carrageenan gum, Gellan gum, alginates and agar. The composition of the reservoir preferably developed for use in the current invention includes a gel forming agent, water, fragrance, suitable co-solvents and surfactants and may further include as other optional constituents, gelling aids such as locust bean and xanthan gum and carboxymethyl cellulose as well as additional components such as potassium chloride, preservatives, freeze-thaw stabilizers and coloring additives.

A typical formula representative of the type suitable for use in the present invention would be represented by the following:

| Ingredients | Percents (by weight) |
| --- | --- |
| Water | 89.85 |
| Kelcogel AFT[1] | 0.64 |
| Sodium Citrate | 0.16 |
| Locust Bean Gum | 0.25 |
| Carboxymethyl Cellulose | 0.60 |
| Potassium Chloride | 0.30 |
| Dipropylene Glycol | 5.00 |
| Preservative, Color_ | 0.20 |
| Fragrance | 3.00 |
|  | 100.00 |

[1]Kelcogel AFT, KELCO Industrial Biopolymers, Monsanto Company

In accordance with an aspect of the present invention and in its preferred form, a dispensing container for solid air treating gels has a base container, which constitutes the gel housing and is configured with rigid sidewalls and a fully opened top and a base in which there is a smaller opening to permit filling. In addition, a rigid or a semi-rigid grille like apertured member is inserted and permanently attached in a single plane across the major opening at or near the uppermost part of that previously described gel housing. Whereas the grille is optimally created from a plastic composition, the base could be made from any other suitable rigid or semi-rigid free standing material including glass, ceramic or terra cotta, or other suitable clay like material. The opportunity of using a transparent or translucent container as would be the condition with a plastic or glass housing facilitates the observation as to the amount of the gel reservoir, which remains in the container. Alternatively, when the unit is manufactured from plastic, the grille assembly could be integrally molded into the unit during the plastic fabrication process. Finally, a cover is provided and adapted to both receive and slidably engage the uppermost part of the gel housing. It is to be appreciated that the cover and base may include cooperating beveled surface portions, which when the cover is fully engaged with the base the beveled surface portions serve to prevent any liquid loss during filling, or the unwanted loss of the air treating agents when the container is stored or in transit. When the cover is removed the unit is activated and the release of the fragrance and co-evaporants is commenced.

According to the invention, there is provided a dispensing unit for an air treating gel having releaseable volatilizable components, comprising: a container for holding said air treating gel, having an interior sidewall that, at an end remote from a closed end of said container, defines a major opening; and, an aperture member fast with said interior sidewall adjacent said major opening, said aperture member being sized to support an emanating surface of said gel which remains adjacent to the major opening of said container during the release of said volatilizable components through said major opening by way of said aperture member.

According to the invention, there is also provided a dispensing unit for an air treating gel having releaseable volatilizable components, comprising: a container for holding said air treating gel, having an interior sidewall that, at an end remote from a closed end of said container, defines a major opening; an aperture member, having a gel supporting grille, engaging said interior sidewall adjacent said major opening, said grille being sized to support an emanating surface of said gel which remains adjacent to the major opening of said container during the release of said volatilizable components; and, a removable lid closing said major opening, said lid having an elevation above said major opening, said elevation defining an uppermost limit of said emanating surface of said gel.

According to the invention, there is also provided a method of providing vacuum relief to a dispensing unit for an air treating gel having releasable volatilizable components, comprising the steps of: a) providing a container for holding said air treating gel, having an interior sidewall that, at an end remote from a closed end of said container, defines a major opening, with an aperture member fast with said interior sidewall adjacent said major opening to support an emanating surface of said gel which remains adjacent to the major opening of said container during the release of said volatilizable components; and b) providing a space between the interior sidewall and said aperture member to provide vacuum relief to the dispensing unit when filled with said gel and activated by exposing said emanating surface to the surrounding environment.

BRIEF DESCRIPTION OF THE DRAWINGS

The invention will now be described, by way of example, with reference to the accompanying drawings, in which.

DETAILED DESCRIPTION OF THE INVENTION

Figure 1:
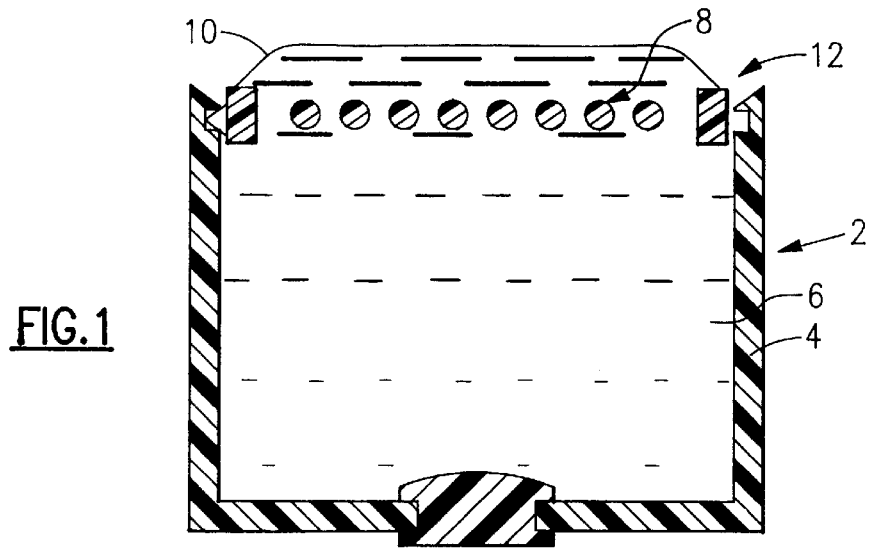
FIG. 1 is a diagrammatic cross-section of a filled dispenser with the cover cap removed shown upright at the time of activation to commence the dispensation of volatile components therefrom.

As illustrated in FIG. 1, a dispensing unit 2 of the present invention uses a plastic gel housing or container 4 to hold an air treating gel 6. The container 4 is made of plastic.

Figure 2:
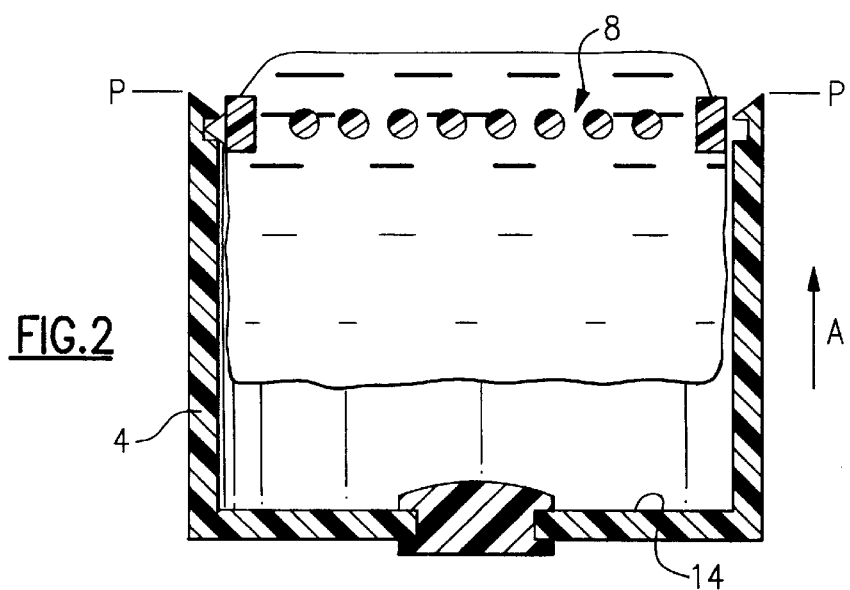
FIG. 2 is a diagrammatic cross-section of the dispenser shown in FIG. 1 after a period of time has elapsed during which volatile components have been dispensed from the gel container.

The container 4 is provided with a grille lattice or grille 8 as a means of attachment for the gel 6 so that an emanating surface 10 of the gel 6, during operation of the dispenser, remains dimensionally intact, stable, and fixed in place. The grille 8 is preferably made from a plastic composition such as polyethylene or polypropylene and is lockably inserted, glued or molded in place, adjacent the inside edge of the major opening 12 of the container 4. Accordingly, the grille 8 also functions to keep the emanating surface 10, as the gel is depleted, in close proximity to a plane P defined by the outer edge of the major opening 12 of the container 4 and the grille 8 (FIG. 2). In this manner the gel's natural tendency to shrink dimensionally in all directions and to recede into the confines of the container is prevented.

Figure 3:
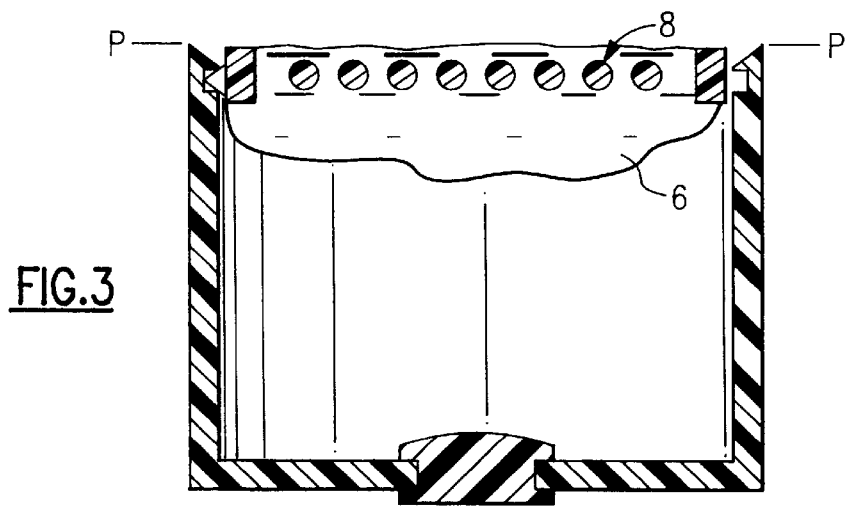
FIG. 3 is a diagrammatic cross-section of the dispenser of FIG. 1 shown when the gel reservoir has been substantially depleted.

It is to be appreciated that the grille 8, due to the support it provides to the gel, allows the use of the dispenser in either an upright orientation, illustrated in FIGS. 1–3, or any other desired orientation, without causing degradation of the emanating surface 10. This results from the fact that, apart from the gel's attachment to the grille, the gel 6 does not attach itself to any interior surface of the container 4 and thus, is free to act as a freely-moving elastic gel reservoir that replenishes the emanating surface 10. As such, it is the continuous movement of the volatile components in the gel's composition which migrate from the gel mass past the grille 8 for eventual evaporation.

As illustrated by FIGS. 1–3, the mass of the gel reservoir shrinks in an upward direction A (FIG. 2) from a bottom interior surface 14 of the container 4 towards the emanating surface 10. Since the shrinkage of the gel reservoir takes place within the confines of the container 4, there is virtually no change in the area of the emanating surface 10, which is in distinct contrast to commercially available units, in which the fully exposed gel shows significant changes dimensionally due to the large degree of shrinkage associated with this type of fragrance diffusing medium. Additionally, it is the dissipation of the volatile components from the gel mass, located within the container 4, that result in the continual collapse of the residual gel matrix which remains behind after the fugitive components have exited. Collapse of the residual gel matrix is attributable to the loss of liquid which upon migration toward the emanating surface 10 no longer provides support for the gel form, resulting in the contracting of the gel body. As such, once all of the volatile components have been depleted, the non-volatile portion of the gel 6 will come to reside very near plane P (FIG. 3). Therefore, it is the movement of the volatile components of the gel 6 past the grille 8 and the continuous contraction of the residual gel composition towards the grille 8 which defines the dynamics which occur in the present invention.

Figure 4:
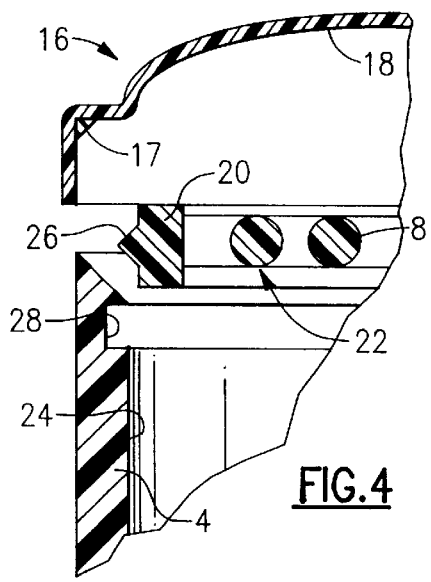
FIG. 4 is a fragmentary sectional view of the portion of the dispenser of FIG. 3 adjacent the opening and prior the engagement of the grille and cover cap.
Figure 5:
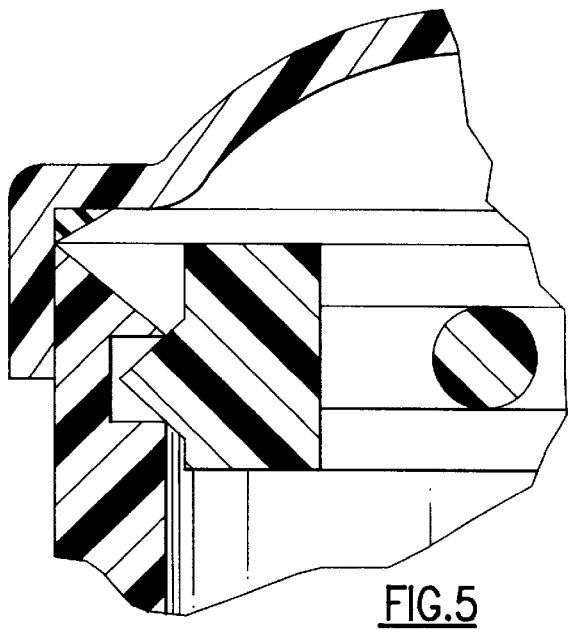
FIG. 5 is an enlarged fragmentary sectional view of the portion of the dispenser of FIG. 3 adjacent the opening with the grille and cover cap suitably engaged.

Turning now to FIGS. 4–5, a cap or lid 16 is provided to enclose and seal the gel 6 within the container 4. The lid 16 is sealingly engageable on the major opening edge 12 of the container 4 by conventional means, and can be made of either plastic or metal. Preferably, the lid is made of plastic with a suitable interference fit for effective sealing. Alternatively the lid could, for example be made of aluminum and use a gasket 17 fitted within the interior of the lid in such a manner that the gasket 17 cooperates with major opening edge 12, to prevent any liquid loss during filling, or the unwanted loss of the air treating agents when the container is stored or in transit. It is to be appreciated that the major opening edge 12 is preferably beveled to provide an improved sealing engagement with the gasket 17. Additionally, the lid 16 may be configured with a slight dome or elevation 18 in its design to keep it raised some small distance (e.g. ¼ inch) above the plane P (FIG. 5). In this manner, during filling of the container 4 through a filling hole 30 (FIG. 10) a small quantity of gel 6 will occupy that space created by the dome 18 of the lid above the grille 8, so that upon activation any slight shrinkage which might occur initially in the emanating surface 10, due to evaporative loss, will result in an emanating surface that is substantially flush with the major opening edge 12 of the container 4. To activate the dispenser, the lid 16 is removed from the major opening edge 12, for example, preferably by a pull tab (not shown) that releases the lid from the container 4, thereby exposing the emanating surface 10 of the gel to the surrounding atmosphere and allowing the volatile components of the gel 6 to evaporate from the emanating surface.

In the preferred embodiment, the grille 8 is a semi-rigid plastic that is surrounded and supported by a rigid plastic ring 20 to form a single aperture member 22. Alternatively, the grille 8 and the ring 20 could be molded together to form the aperture member 22 or the aperture member 22 could be integrally molded into the unit during the plastic fabrication process. The aperture member 22 is engagable with an interior sidewall 24 of the container 4, and is preferably held lockably in place by a mechanical interlock. The mechanical interlock comprises three or more projections 26 on the ring 20, which lock into place when pushed into contact with a continuous circumferential recess 28 in the interior sidewall 24 running adjacent the major opening edge 12 of the container 4. Alternatively, the aperture member 22 could be glued in place adjacent and flush with the major opening edge of a container with or without a continuous circumferential recess in the interior sidewall.

Figure 9:
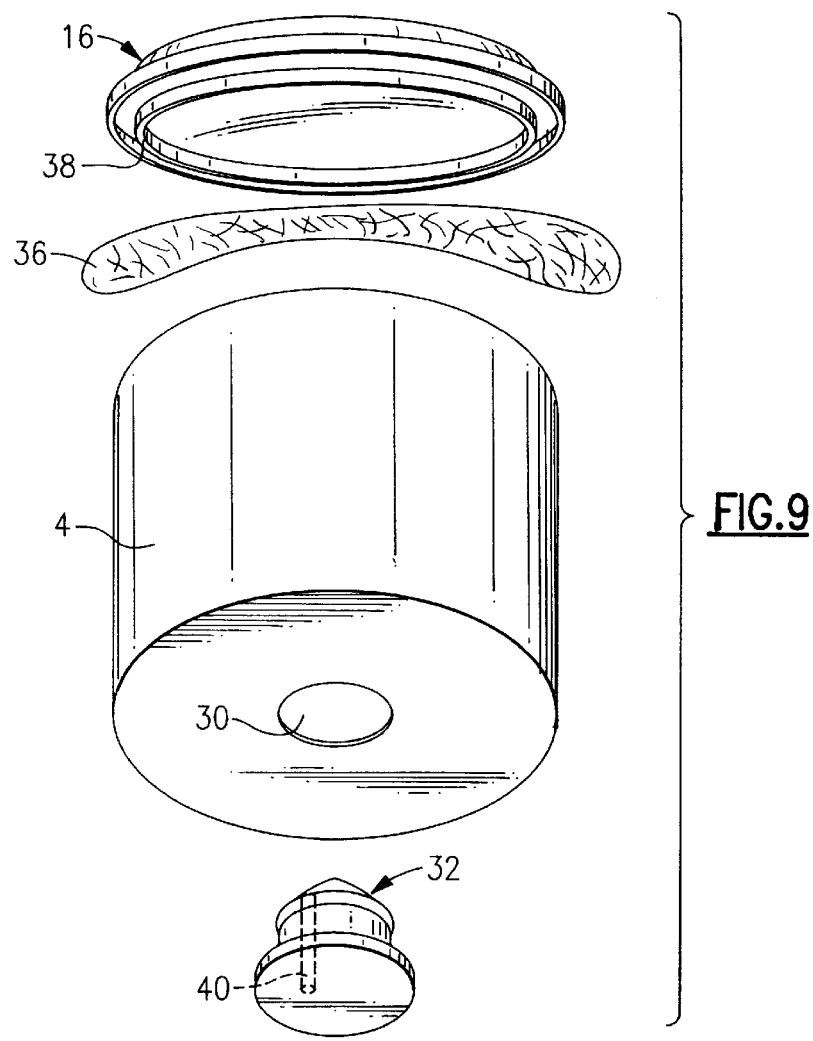
FIG. 9 is an exploded perspective view of an embodiment of the dispenser in which a textile is used as the means for gel attachment.

The aperture member 22 is centered within the major opening of the unit by the contact of the projections 26 with the interior sidewall 24 thereby creating a small annular space of approximately 1/16 inch between the aperture member 22 and the interior sidewall 24 of the container 4. This small annular space between the flange and the interior sidewall 24 (except where contact is made by the projections 26 on the ring 20), creates a volume which becomes filled by liquid gel during a hot fill process, discussed hereafter, and which then sets to form the solid gel 6. However, since the gel portion contained within this annular space is limited, when the unit 2 is activated and evaporation begins, this gel portion shrinks enough to open a small separation between the gel and the interior sidewall 24 of the container 4. This separation permits air to re-enter the container 4, passing through the small separation, to inevitably reach the bottom of the dispenser thereby providing for vacuum relief. Units manufactured in this format could also be fabricated without the need for a bottom fill hole 30 and sealing plug 32 (FIG. 9). Instead, units would be filled from the top, capped and immediately inverted while the gel is still in its fluid liquified state. Alternative formats also exist where the grille 8 and ring 20 are locked into place across the major opening of the unit 2, without the benefit of an annular space between the flange 20 and container sidewall 24. In such an alternative disposition, vacuum relief would then be achieved through the use of a vent hole 40 which passes through a plug 32 used to close fill hole 30 on the bottom of the unit 2.

Figure 6:
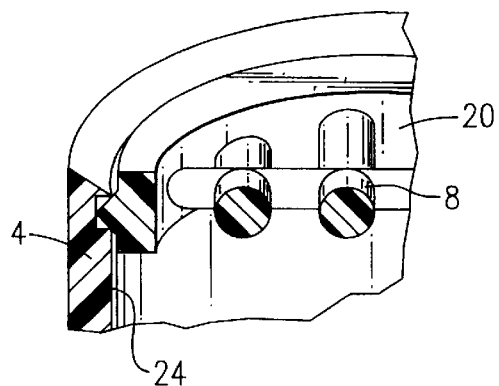
FIG. 6 is a perspective fragmentary sectional view of the dispenser according to the present invention shown empty prior to filling shown without the lid displayed.
Figures 7A, 7B:
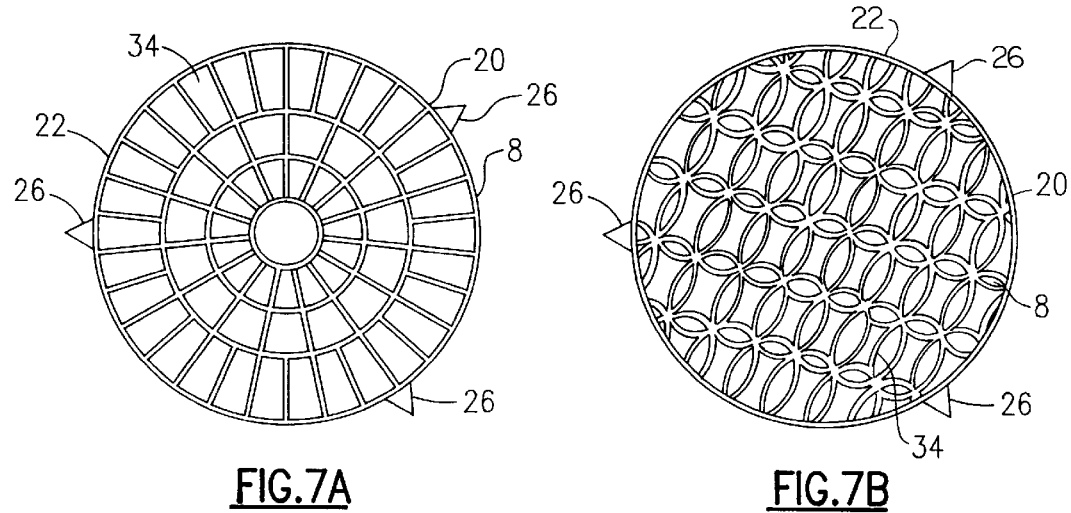
FIGS. 7A and 7B show exemplary configurations for the grille member.
Figure 8:
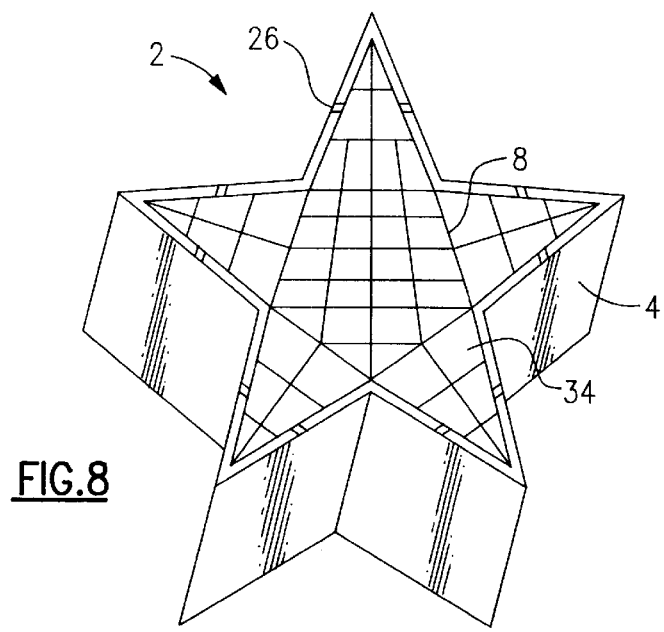
FIG. 8 is a perspective view of the dispenser illustrating another packaging design option in this instance, a star-like configuration.

In FIGS. 6–8, the apertures 34 in the grille 8 need be of sufficient size to permit the heated liquified air freshening gel 4 to pass freely through during the hot fill process. However, the apertures 34 must also be small enough so as to provide a sufficient means of support and attachment for the gel 4, once the gel has solidified and intimately surrounded the aperture member 22, from both above and below as well as from side to side, within the solid gel matrix. It is also important, in the process of selecting a suitable grille design, that the openings are sufficiently large that the grille 8 does not present an occlusive obstruction and impede the upward migration of the volatile components toward the emanating surface 10. It is also of importance that the grille function in such a way such as not to sever or disrupt the continuous moving nature of the gel reservoir from the emanating portion of the gel. Typically, apertures 34 on the order of ⅛ inch to ⅜ inch in transverse dimension (e.g. square), with cross members approximately 1/16 inch to ⅛ inch wide (e.g. diameter), have proven to be effective in providing sufficient attachment to keep the emanating surface 10 fully expanded, as well as providing sufficient support so as to keep the gel reservoir suspended from the grille. Although the pattern of the grille 8, illustrated in FIG. 6, has been illustrated as a cross hatch of spaced interlocking horizontal and longitudinal members, it will be appreciated that any number of pattern designs would suffice to achieve the same purpose. Such patterns include, and are not limited to, a spoke configuration (FIG. 7A) and joined concentric rings (FIG. 7B). Additionally, it is to be appreciated that the container 4 and the aperture member 22 can also be formed into other desirable shapes, such as a star as illustrated by FIG. 8, without departing from the intent of the present invention.

As illustrated in FIG. 9, the grille 8 can be replaced by a woven or non-woven textile. In this manner the loose entanglement of the fibers in a porously configured woven or non-woven textile 36 provides a matrix with sufficient porosity, to provide a source of attachment for the gel and yet is not occlusive to the point that the migration of fugitive materials is inhibited. Units have been successfully prepared using non-woven fabrics, with either mechanically entangled or adhesively bound fibers with materials ranging from 1/16 to 1/4 inches thick with weights on the order of 4 ounces to 15 ounces per square yard.

In the unit 2 of FIG. 9, the textile 36 is held in place by the use of a retainer ring 38, which circumferentially engages the interior sidewall of the container 4, by way of the textile 36, so that the textile 36 fully covers the major opening of the container and is supported in place. Again, as in the previous examples, a domed cover cap 16 is placed on the unit 2 prior to filling which allows for the formation of approximately 1/4 inch, for example, of the gel on top of the porous textile 36 to ensure that the emanating surface 10 remains flush with the plane P defined by the major opening of the container 4 and fully embeds the woven or non-woven fabric within the gel matrix. This methodology would require a venting mechanism which is presented by the vent 40 extending through the plug 32 of the container 4.

Figure 10:
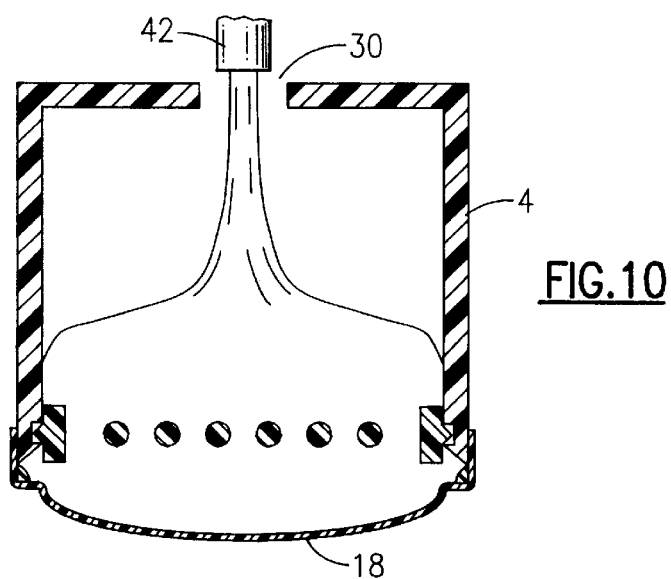
FIG. 10 is a diagrammatic cross-section of the dispenser of FIGS. 1–3 shown inverted in the process of being filled, with the cover cap in place.

FIG. 10 illustrates the hot filling process is shown by example only using a unit with a grille 8. First, the hot fill process entails providing an inverting lidded container 4. Second, the gel composition, heated until liquified, is allowed to flow, by the use of a nozzle 42, through the filling hole 30 into the inverted lidded container. Last, the filling hole is sealingly closed with the plug 32 when the container is filled with an desired amount of gel 6. A similar process can be used with a container having a fabric grille and a vented plug.

Sensory evaluations were conducted in order to subjectively quantify the performance differences between two units, one of which incorporated the methodology disclosed herein and another identical container was fabricated without a grille 8 and was treated as the control.

Figure 11A:
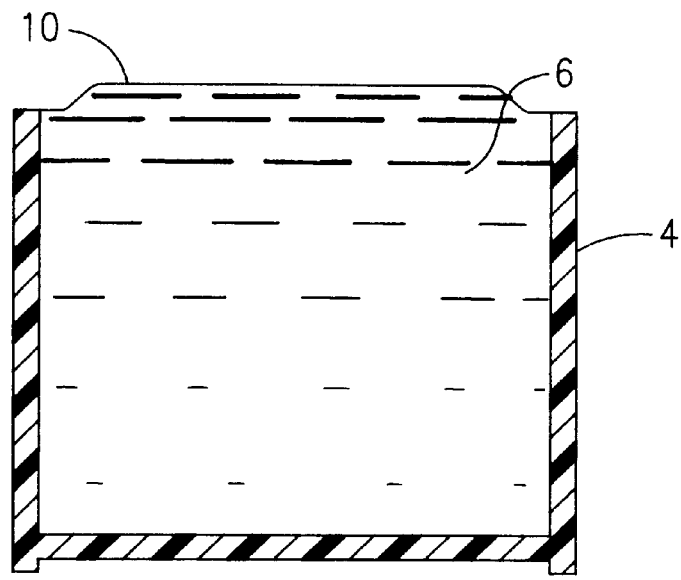
FIG. 11A and 11B are both a side view of a prior art dispenser with the emanating surface exposed shown filled and depleted, respectively.
Figure 11B:
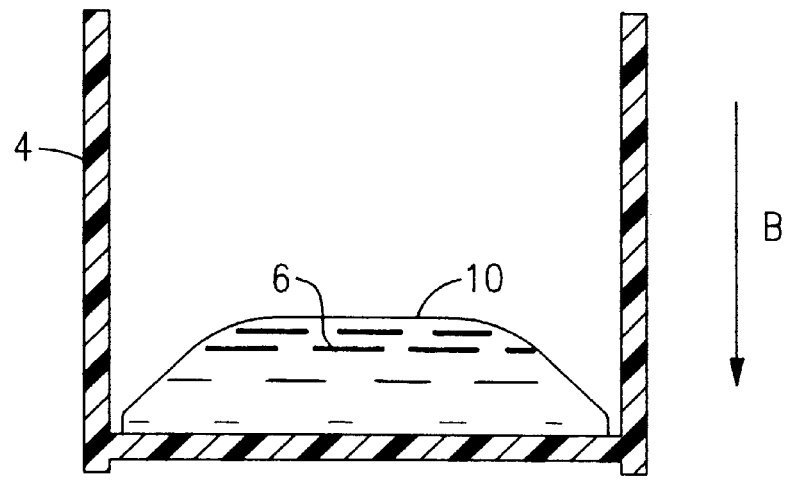

Sensory testing was conducted as follows:

Units were prepared, according to the format described in FIG. 1, as well as a control unit of equal size prepared in according with the prior art configuration detailed in FIG. 11A. It should be noted that the prior art unit depletes in the direction of B as depicted in FIG. 11B. The units were then filled, utilizing the gel formulation, presented herein as Formula I. The units had identical fill weights (180 grams) and contained a Raspberry fragrance (Wessel Fragrances WS 6907) at a 3 percent loading. The opening on each unit was 2.5 inches in diameter, creating an exposed gel surface of 4.9 square inches. The units were uncapped and permitted to run continually for a period of four weeks in an ambient environment, maintained at 73–75° F. Units were concealed behind a cardboard shield to prevent any visual bias and placed in 12 cubic feet smelling boxes equipped with a smelling port for a period of 30 minutes, prior to being evaluated by a trained sensory evaluation panel of 10 evaluators.

After the units had been opened, the evaluation comparison of the two units was conducted on days 1, 7, 14 and 28. The panelists were asked to compare the intensities of the two units where Unit G (present embodiment, FIG. 1) and Unit H (control, FIG. 11) were rated given the following choices:

Unit G stronger than Unit H
Unit H stronger than Unit G
Unit G and Unit H are of equal strength The results are as follows:

| Day | Unit G According to FIG. 1 Strength Preference (G Stronger than H) Respondents | Unit H According to FIG. 11 (Control) Strength Preference (H Stronger than G) Respondents | Equal Strength Respondents |
| --- | --- | --- | --- |
| 1 | 1 | 2 | 7 |
| 7 | 2 | 2 | 6 |
| 14 | 6 | 1 | 3 |
| 21 | 9 | 0 | 1 |
| 28 | 10 | 0 | 0 |

It can be seen that in the early days (days 1–7) of the newly exposed units that they exhibit little difference in intensity since the control unit and the current embodiment prototype are essentially the same at this time. However, as the units age, differences in performance become more noticeable with Unit G significantly out performing Unit H (control).

The negative effects upon the performance of the control unit, as a function of time, results in a diminished emanating surface 10, as well as an emanating surface 10 which has sunken into the confines of the container 4, where it is no longer susceptible to the ambient air currents so important for the circulation of the fragrance materials into the surrounding air. This effect becomes more pronounced as the unit ages with weeks three and four clearly demonstrating the performance advantages represented by the device and methodology disclosed herein.

Wherefore, I claim:

1. A dispensing unit for an air treating gel having releasable volatilizable components, comprising:

a container for holding said air treating gel, having an interior sidewall that, at an end remote from a closed end of said container, defines a major opening; and, an aperture member fast with said interior sidewall adjacent said major opening, said aperture member having a grill of at least semi-rigid material and being sized to support an emanating surface of said gel which remains adjacent to the major opening of said container during the release of said volatilizable components through said major opening by way of said aperture member;

wherein the grill defines a plurality of member defining apertures.

2. The dispensing unit of claim 1, wherein the apertures are within a range of 1/8 inch to 3/8 inch in transverse dimension, and cross members defining the grill have a cross-section in a range of 1/16 inch to 1/8 inch wide.

3. The dispensing unit of claim 1, wherein the aperture member is a rigid, self-supporting structure.

4. The dispensing unit of claim 1, wherein cross members of the grill are a semi-rigid material supported within a rigid frame to form a self-supporting aperture member.

5. The dispensing unit of claim 1, wherein the aperture member includes at least three projections that lockably engage an annular recess in said sidewall adjacent said major opening.

6. The dispensing unit of claim 5, wherein the aperture member is sized such that, when the at least three projections are engaged in said recess, a separation of approximately 1/16 of an inch is maintained between said aperture member and said sidewall.

7. The dispensing unit of claim 1, wherein said sidewall has a beveled edge that defines the major opening of said container.

8. The dispensing unit of claim 7, wherein a lid sealingly engages said beveled edge.

9. The dispensing unit of claim 8, wherein said lid has a domed portion to provide a space between the lid and the aperture member.

10. The dispensing unit of claim 3, wherein the aperture member is formed integrally with said container adjacent to said major opening of said container.

11. A method of providing vacuum relief to a dispensing unit for an air treating gel having releasable volatilizable components, comprising the steps of:

a) providing a container for holding said air treating gel, having an interior sidewall that, at an end remote from a closed and of said container, defines a major opening, with an aperture member, having an at least semi-rigid grill, fast with said interior sidewall adjacent said major opening to support an emanating surface of said gel which remains adjacent to the major opening of said container during the release of said volatilizable components; and b) providing a space between the interior sidewall and said aperture member to provide vacuum relief to the dispensing unit when filled with said gel and activated by exposing said emanating surface to the surrounding environment.

* * * * *